(12) United States Patent
Irisawa et al.

(10) Patent No.: US 10,499,887 B2
(45) Date of Patent: Dec. 10, 2019

(54) BIOPSY NEEDLE AND PHOTOACOUSTIC MEASUREMENT APPARATUS

(71) Applicant: FUJIFILM Corporation, Tokyo (JP)

(72) Inventors: Kaku Irisawa, Ashigarakami-gun (JP); Dai Murakoshi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 265 days.

(21) Appl. No.: 15/711,239

(22) Filed: Sep. 21, 2017

(65) Prior Publication Data
US 2018/0008243 A1 Jan. 11, 2018

Related U.S. Application Data

(63) Continuation of application No. PCT/JP2016/055235, filed on Feb. 23, 2016.

(30) Foreign Application Priority Data

Mar. 30, 2015 (JP) .................................. 2015-068280

(51) Int. Cl.
*A61B 10/02* (2006.01)
*A61B 17/34* (2006.01)
(Continued)

(52) U.S. Cl.
CPC ........ *A61B 10/0233* (2013.01); *A61B 5/0095* (2013.01); *A61B 5/145* (2013.01);
(Continued)

(58) Field of Classification Search
CPC ............ A61B 10/0233; A61B 10/0275; A61B 17/3403; A61B 2017/00057;
(Continued)

(56) References Cited

U.S. PATENT DOCUMENTS

| 6,053,871 A * | 4/2000 | Cockburn ............ A61B 8/0833 |
| | | 600/459 |
| 2002/0128570 A1* | 9/2002 | Bowman .................. A61B 5/01 |
| | | 600/567 |

(Continued)

FOREIGN PATENT DOCUMENTS

| JP | 7-54855 Y2 | 12/1995 |
| JP | 8-38477 A | 2/1996 |

(Continued)

OTHER PUBLICATIONS

International Preliminary Report on Patentability and Written Opinion of the International Searching Authority (forms PCT/IB/373 and PCT/ISA/237), dated Oct. 3, 2017, for corresponding International Application No. PCT/JP2016/055235, with an English translation of the Written Opinion.

(Continued)

*Primary Examiner* — Eric F Winakur
*Assistant Examiner* — Chu Chuan Liu
(74) *Attorney, Agent, or Firm* — Birch, Stewart, Kolasch & Birch, LLP

(57) ABSTRACT

In a biopsy needle having a hollow tubular outer needle, an inner needle that is disposed in a hollow portion of the outer needle so as to be movable in the tube axis direction relative to the outer needle, and a recessed sample collection portion that is cut inward from a circumferential surface of the inner needle, an inner hole that extends in the longitudinal direction of the inner needle on each of the inner needle distal end side and the inner needle rear end side of the sample collection portion and are opened to the sample collection portion is provided in the inner needle, and a light guide member is disposed in the inner holes. At least a part of the light guide member is fixed by filler filled in the inner holes.

20 Claims, 13 Drawing Sheets

(51) Int. Cl.

| | |
|---|---|
| *G01N 29/24* | (2006.01) |
| *A61B 5/00* | (2006.01) |
| *A61B 5/145* | (2006.01) |
| *G01N 29/22* | (2006.01) |
| *A61B 8/12* | (2006.01) |
| *A61B 8/00* | (2006.01) |
| *A61B 5/06* | (2006.01) |
| *A61B 17/00* | (2006.01) |

(52) U.S. Cl.
 CPC ......... *A61B 5/6848* (2013.01); *A61B 5/6851* (2013.01); *A61B 10/0275* (2013.01); *A61B 17/3403* (2013.01); *G01N 29/22* (2013.01); *G01N 29/2418* (2013.01); *A61B 5/0035* (2013.01); *A61B 5/06* (2013.01); *A61B 8/12* (2013.01); *A61B 8/4416* (2013.01); *A61B 2017/00057* (2013.01); *A61B 2017/3413* (2013.01); *G01N 2291/02475* (2013.01)

(58) Field of Classification Search
 CPC .......... A61B 2017/3413; A61B 5/0035; A61B 5/0095; A61B 5/06; A61B 5/145; A61B 5/6848; A61B 5/6851; A61B 8/12; A61B 8/4416; G01N 2291/02475; G01N 29/22; G01N 29/2418
 See application file for complete search history.

(56) References Cited

U.S. PATENT DOCUMENTS

| | | | |
|---|---|---|---|
| 2004/0131299 A1* | 7/2004 | Adoram | A61B 8/0833 385/12 |
| 2008/0221456 A1* | 9/2008 | Babchenko | A61B 5/0075 600/476 |
| 2010/0135111 A1* | 6/2010 | Bates | A61B 5/0097 367/11 |
| 2015/0297092 A1 | 10/2015 | Irisawa | |
| 2015/0335289 A1 | 11/2015 | Irisawa et al. | |
| 2015/0359525 A1* | 12/2015 | Hendriks | A61B 5/6848 600/478 |
| 2016/0135689 A1 | 5/2016 | Murakoshi | |

FOREIGN PATENT DOCUMENTS

| | | |
|---|---|---|
| JP | 11-33029 A | 2/1999 |
| WO | WO 2012/169178 A1 | 12/2012 |
| WO | WO 2014/109148 A1 | 7/2014 |
| WO | WO 2014/148379 A1 | 9/2014 |
| WO | WO 2015/015932 A1 | 2/2015 |

OTHER PUBLICATIONS

International Search Report (form PCT/ISA/210), dated Apr. 19, 2016, for corresponding International Application No. PCT/JP2016/055235, with an English translation.

* cited by examiner

FIG. 4A
FIG. 4B
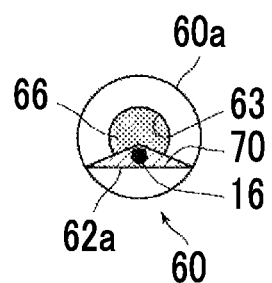
4A-4A
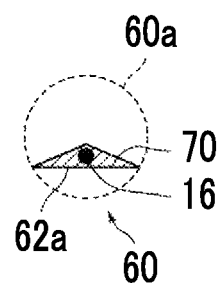
4B-4B 7A-7A 7B-7B

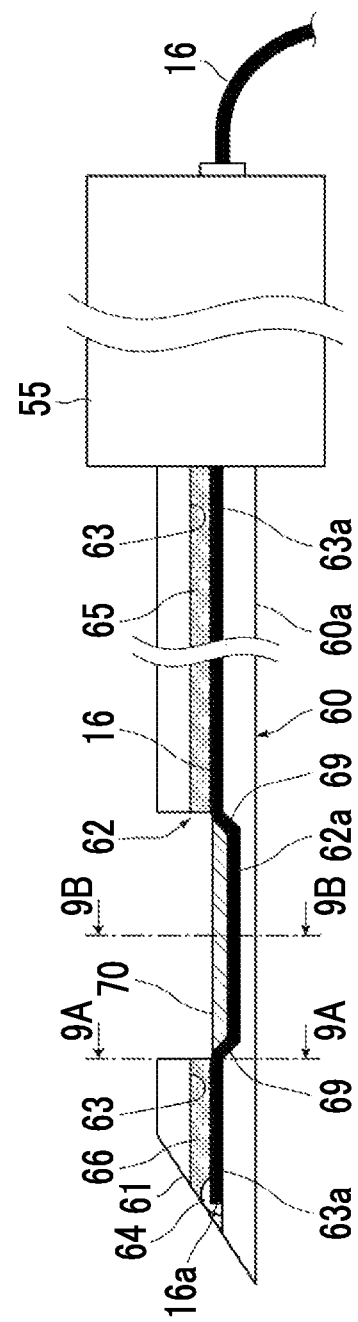

9A-9A 9B-9B

BIOPSY NEEDLE AND PHOTOACOUSTIC MEASUREMENT APPARATUS

CROSS-REFERENCE TO RELATED APPLICATIONS

This application is a Continuation of PCT International Application No. PCT/JP2016/055235 filed on Feb. 23, 2016, which claims priority under 35 U.S.C § 119(a) to Japanese Patent Application No. 2015-068280 filed on Mar. 30, 2015. Each of the above application(s) is hereby expressly incorporated by reference, in its entirety, into the present application.

BACKGROUND OF THE INVENTION

1. Field of the Invention

The present invention relates to a photoacoustic measurement apparatus that emits light toward a subject and receives the light to detect photoacoustic waves generated within the subject.

In addition, the present invention relates to a biopsy needle used in the photoacoustic measurement apparatus.

2. Description of the Related Art

In recent years, a non-invasive measurement method using a photoacoustic effect has been drawing attention. In the measurement method, a photoacoustic wave, which is an elastic wave generated as a result of emission of pulsed light having an appropriate wavelength (for example, a wavelength band of visible light, near-infrared light, or intermediate infrared light) to a subject and absorption of the energy of the pulsed light by an absorbing substance in the subject, is detected to quantitatively measure the concentration of the absorbing substance. The absorbing substance in the subject is, for example, glucose or hemoglobin contained in blood. In addition, a technique of detecting such a photoacoustic wave and generating a photoacoustic image based on the detection signal is called photo acoustic imaging (PAI) or photo acoustic tomography (PAT).

Conventionally, surgery, sample collection, and treatment such as chemical injection have been performed by inserting various insertion needles into a subject that is a living body. As one type of such an insertion needle, for example, as shown in JP1996-38477A (JP-H08-38477A) and JP1999-33029A (JP-H11-33029A), a biopsy needle including a hollow tubular outer needle and an inner needle, the inner needle is disposed in the hollow tube of the outer needle so as to be relatively movable in the tube axis direction, is known. The biopsy needle has a recessed sample collection portion, which is cut inward from the circumferential surface of the inner needle, in the inner needle. After the inner needle and the outer needle are inserted into the subject, the relative movement is performed to cut a living tissue, and the living tissue is held in the sample collection portion.

In the case of performing various treatments using such an insertion needle, it is desirable to be able to check the distal end position of the insertion needle for the safety of the subject. WO2014/109148A discloses a technique that enables checking the distal end position of an insertion needle by applying the photo acoustic imaging described above. In this technique, a light guide member, such as an optical fiber, is disposed in the insertion needle so as to reach the vicinity of the distal end of the insertion needle, and a light absorber that covers the distal end of the light guide member is disposed, so that light propagated through the light guide member is incident on the light absorber from the distal end of the light guide member. Therefore, in the case of performing various treatments using the insertion needle, the distal end of the light guide member, that is, the distal end of the insertion needle can be checked by making the light incident on the light absorber from the distal end of the light guide member to generate photoacoustic waves from the light absorber, detecting the photoacoustic waves, and displaying a photoacoustic image of the light absorber.

On the other hand, JP1995-54855Y (JP-H07-54855Y) has proposed that, in order to acquire a photoacoustic image of a sample in a sample collection portion of an insertion needle (needle-shaped applicator), an optical fiber is inserted into the insertion needle between the rear end of the insertion needle and the sample collection portion, and light is emitted to the sample from the distal end of the optical fiber exposed in the sample collection portion.

SUMMARY OF THE INVENTION

In the case of inserting a biopsy needle having a sample collection portion into the subject, it has been requested to correctly check the position of the biopsy needle using photo acoustic wave imaging, photo acoustic tomography, or the like.

In this regard, JP1995-54855Y (JP-H07-54855Y) discloses a technique of arranging the light guide member up to the sample collection portion. However, since the biopsy needle is usually inserted into the subject in a state in which the sample collection portion is covered with the outer needle, it is not possible to correctly check the position of the biopsy needle.

The present invention has been made in view of the above circumstances, and it is an object of the present invention to provide a biopsy needle whose position can be correctly checked using photo acoustic wave imaging, photo acoustic tomography, or the like.

In addition, it is an object of the present invention to provide a photoacoustic measurement apparatus including such a biopsy needle.

A biopsy needle according to an aspect of the present invention comprises: a hollow tubular outer needle; an inner needle that is movable in a tube axis direction relative to the outer needle and that is disposed in a hollow tube of the outer needle; a sample collection portion that is provided on a circumferential surface of the inner needle, and has a recessed shape; an inner hole that is provided on each of a distal end side and a rear end side of the inner needle the sample collection portion in the inner needle and that extends in the tube axis direction of the inner needle; a first light guide member that is disposed in the inner hole and that is disposed from the rear end side of the inner needle to vicinity of the distal end of the inner needle; a first light absorber that absorbs light emitted from a distal end of the first light guide member and emits a photoacoustic wave; and a filler that is filled in the inner hole to fix at least a part of the first light guide member.

In the biopsy needle according to an aspect of the present invention that has the above-described configuration, it is preferable that the first light guide member is fixed to a bottom surface of the sample collection portion by a fixing member that covers at least a part of the first light guide member.

In the biopsy needle according to an aspect of the present invention, it is preferable that a bottom surface of the inner hole and a bottom surface of the sample collection portion are located at the same height position. The "height position" refers to top and bottom positions in a vertical direction in a state in which the biopsy needle is disposed such that the bottom surface of the sample collection portion faces the top side in the vertical direction.

Alternatively, a bottom surface of the sample collection portion may be located at a position lower than a bottom surface of the inner hole. In the case of such a configuration, it is preferable that at least one of an end portion of the bottom surface of the sample collection portion on an inner needle distal end side or an end portion of the bottom surface of the sample collection portion on an inner needle rear end side has an inclined surface whose height changes continuously. The above "position lower than a bottom surface of the inner hole" also refers to a position according to the "height position" defined above.

In the biopsy needle according to an aspect of the present invention, it is preferable that the filler filled in the inner hole provided on the distal end side of the sample collection portion in the inner needle also serves as the first light absorber.

In the biopsy needle according to an aspect of the present invention, in addition to the first light guide member described above, it is preferable to further comprise: a second light guide member that is disposed in the inner hole provided on the rear end side of the sample collection portion in the inner needle and that has a distal end located in the sample collection portion; and a second light absorber that absorbs light emitted from the distal end of the second light guide member and emits a photoacoustic wave.

In the case of such a configuration, it is preferable that the second light guide member is fixed to a bottom surface of the sample collection portion by a fixing member that covers at least a part of the second light guide member.

It is preferable that the fixing member that covers at least a part of the second light guide member as described above also serves as the second light absorber.

On the other hand, a photoacoustic measurement apparatus according to an aspect of the present invention comprises the biopsy needle according to the present invention described above.

In the biopsy needle according to the present invention, the distal end of the light guide member can be disposed up to the vicinity of the distal end of the inner needle. Therefore, in the case of inserting the biopsy needle into the subject, it is possible to correctly check the position of the biopsy needle using photo acoustic wave imaging, photo acoustic tomography, or the like.

BRIEF DESCRIPTION OF THE DRAWINGS

FIGS. 4A and 4B are cross-sectional views of the biopsy needle of the first embodiment taken along the lines 4A-4A and 4B-4B in FIG. 3, respectively.

FIG. 8 is a side sectional view showing a biopsy needle according to a fourth embodiment of the present invention.

DESCRIPTION OF THE PREFERRED EMBODIMENTS

Hereinafter, embodiments of the present invention will be described in detail with reference to the diagrams.

Figure 1:
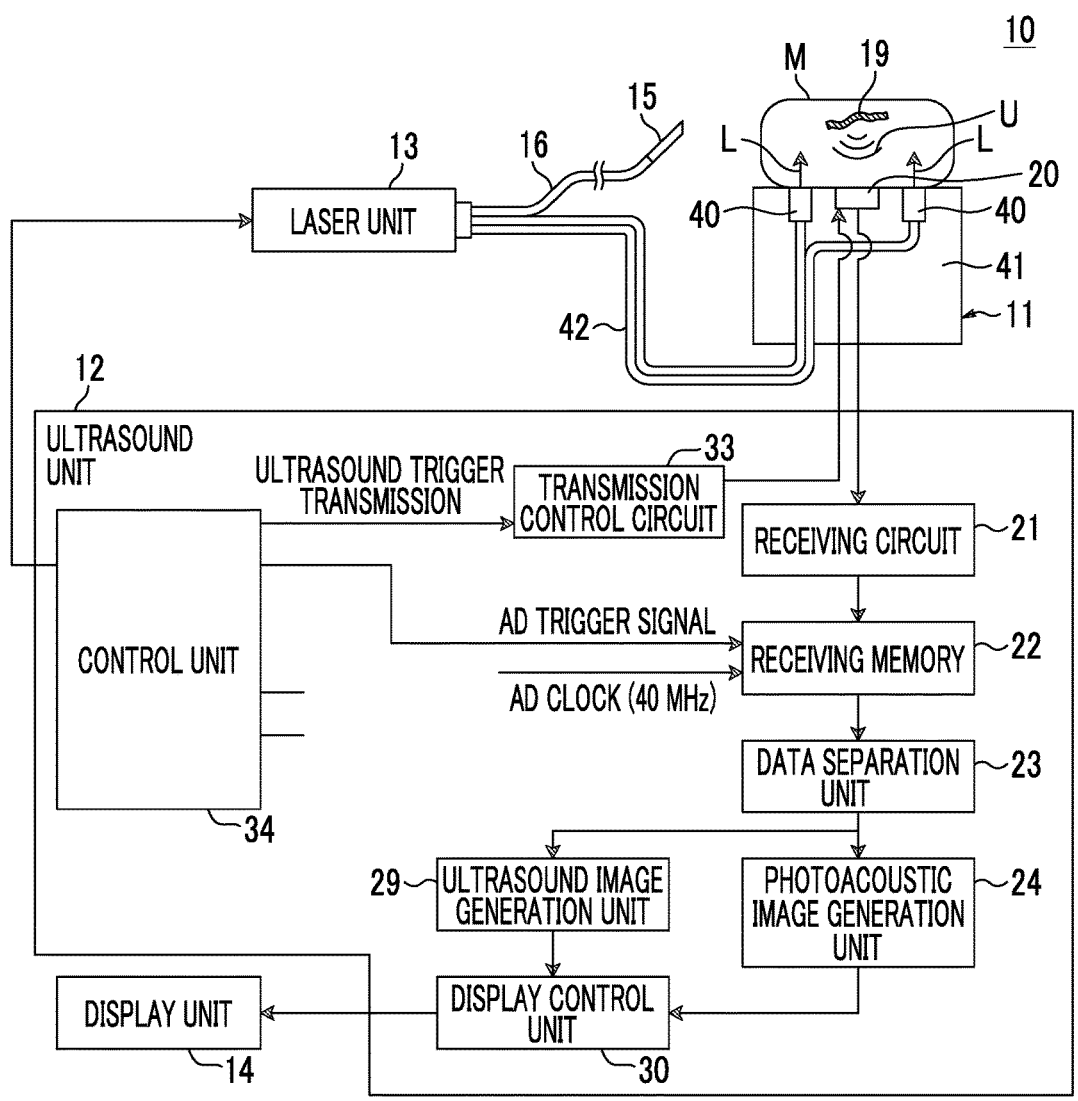
FIG. 1 is a schematic diagram showing the overall configuration of a photoacoustic measurement apparatus according to an embodiment of the present invention.

First, a photoacoustic measurement apparatus that is an embodiment of the present invention will be described. FIG. 1 is a schematic diagram showing the overall configuration of a photoacoustic measurement apparatus 10 of the present embodiment. In FIG. 1, the shapes of a probe 11 and a biopsy needle 15, which will be described later, are schematically shown.

As an example, the photoacoustic measurement apparatus 10 of the present embodiment has a function of generating a photoacoustic image based on a photoacoustic signal, and includes the probe (ultrasound probe) 11, an ultrasound unit 12, a laser unit 13, a display unit 14, the biopsy needle 15, and the like as schematically shown in FIG. 1. Hereinafter, these components will be described in a sequential manner.

The probe 11 has, for example, a function of emitting measurement light and an ultrasound wave toward a subject M, which is a living body, and a function of detecting an acoustic wave U propagating through the subject M. That is, the probe 11 can emit (transmit) ultrasound waves to the subject M and detect (receive) reflected ultrasound waves (reflected acoustic waves) that return due to reflection from the subject M. The probe 11 can also detect photoacoustic waves generated in the subject M. In this specification, the term "acoustic wave" is a term including ultrasound waves and photoacoustic waves. Here, the "ultrasound wave" means an elastic wave transmitted by a probe and a reflected wave of the elastic wave, and the "photoacoustic wave" means an elastic wave emitted by absorbing measurement light by the absorber 19. As the absorber 19 in the subject M, for example, blood vessels, a metal member, and the like can be mentioned.

The probe 11 includes a transducer array 20 that is an acoustic wave detection element, a total of two light emitting units 40 disposed on both sides of the transducer array 20 with the transducer array 20 interposed therebetween, and a housing 41 in which the transducer array 20 and the two light emitting units 40 are housed.

In the present embodiment, the transducer array 20 also functions as an ultrasound wave transmission element. The transducer array 20 is connected to an ultrasound wave transmission circuit in a transmission control circuit 33 and an acoustic wave receiving circuit in a receiving circuit 21 through a wiring line 20a. An optical fiber 42 for guiding laser light L, which is measurement light emitted from the laser unit 13 to be described later, to the light emitting unit 40 is connected to the probe 11.

The transducer array 20 is configured to include a plurality of ultrasound transducers arranged in a one-dimensional or two-dimensional manner, for example. The ultrasound transducer is, for example, a piezoelectric element formed of a polymer film, such as piezoelectric ceramics or polyvinylidene fluoride (PVDF). The ultrasound transducer has a function of converting the received acoustic wave U into an electrical signal. The electrical signal output from the transducer array 20 is input to the receiving circuit 21 to be described later. Generally, the probe 11 corresponding to sector scanning, the probe 11 corresponding to linear scanning, the probe 11 corresponding to convex scanning, and the like are prepared. Among these, an appropriate one selected according to an imaging part is used. The transducer array 20 may include an acoustic lens.

The ultrasound transducer also has a function of transmitting ultrasound waves. That is, in a case where an alternating voltage is applied to the ultrasound transducer, the ultrasound transducer generates ultrasound waves having a frequency corresponding to the frequency of the alternating voltage. Transmission and reception of ultrasound waves may be separated from each other. That is, for example, ultrasound waves may be transmitted from a position different from the probe 11, and reflected ultrasound waves of the transmitted ultrasound waves may be received by the probe 11.

The light emitting unit 40 is a unit that emits the laser light L guided by the optical fiber 42 to the subject M. In the present embodiment, the two light emitting units 40 are disposed on both sides of the transducer array 20, for example, in the elevation direction (in a case where a plurality of ultrasound transducers are arranged in a one-dimensional manner, a direction that is perpendicular to the arrangement direction and is parallel to the detection surface) with the transducer array 20 interposed therebetween.

The laser unit 13 has, for example, a flash lamp excitation Q-switch solid state laser, such as a Q-switch alexandrite laser, and emits the laser light L as measurement light that is emitted to the subject M. The laser unit 13 is configured to receive a trigger signal from a control unit 34 of the ultrasound unit 12 and output the laser light L, for example. It is preferable that the laser unit 13 outputs the pulsed laser light L having a pulse width of 1 to 100 nsec (nanoseconds).

The wavelength of the laser light L is appropriately selected according to the light absorption characteristics of the absorber 19 in the subject M that is a measurement target. For example, in a case where the measurement target is hemoglobin in the living body, that is, in the case of imaging blood vessels, it is generally preferable that the wavelength is a wavelength belonging to the near-infrared wavelength range. The near-infrared wavelength range means a wavelength range of approximately 700 nm to 850 nm. However, it is natural that the wavelength of the laser light L is not limited thereto. In addition, the laser light L may have a single wavelength, or may include a plurality of wavelengths of, for example, 750 nm and 800 nm. In a case where the laser light L includes a plurality of wavelengths, light beams having these wavelengths may be simultaneously emitted to the subject M, or may be emitted while being switched alternately.

In addition to the alexandrite laser described above, the laser unit 13 can be formed by using a YAG-second harmonic generation (SHG)-optical parametric oscillation (OPO) laser, a Ti-Sapphire (titanium-sapphire) laser, or the like capable of outputting laser light in the near-infrared wavelength range similarly.

The optical fiber 42 guides the laser light L emitted from the laser unit 13 to the two light emitting units 40. The optical fiber 42 is not particularly limited, and known fibers, such as a quartz fiber, can be used. For example, one thick optical fiber may be used, or a bundle fiber in which a plurality of optical fibers are bundled may be used. As an example, in a case where a bundle fiber is used, the bundle fiber is arranged so that the laser light L is incident from the light incidence end surface of a group of fiber portions, and the light emitting units 40 are coupled to the light emitting end surfaces of the two branched fiber portions of the bundle fiber.

The ultrasound unit 12 has the receiving circuit 21, a receiving memory 22, a data separation unit 23, a photoacoustic image generation unit 24, an ultrasound image generation unit 29, a display control unit 30, the transmission control circuit 33, and the control unit 34.

The control unit 34 controls each unit of the photoacoustic measurement apparatus 10, and includes a trigger control circuit (not shown) in the present embodiment. The trigger control circuit transmits an optical trigger signal to the laser unit 13, for example, in the case of acquiring a photoacoustic image. As a result, the flash lamp of the excitation source is turned on in the Q-switch solid state laser of the laser unit 13, and excitation of the laser rod is started. While the excitation state of the laser rod is maintained, the laser unit 13 is ready to output the laser light L.

Thereafter, the control unit 34 transmits a Q-switch trigger signal to the laser unit 13 from the trigger control circuit. That is, the control unit 34 controls the output timing of the laser light L from the laser unit 13 using the Q-switch trigger signal. The control unit 34 transmits a sampling trigger signal to the receiving circuit 21 in synchronization with the transmission of the Q-switch trigger signal. This sampling trigger signal specifies the sampling start timing of the photoacoustic signal in an analog to digital converter (AD converter) of the receiving circuit 21. Thus, it is possible to sample a photoacoustic signal in synchronization with the output of the laser light L by using the sampling trigger signal.

In the case of acquiring an ultrasound image, the control unit 34 transmits an ultrasound wave transmission trigger signal for giving an instruction to transmit ultrasound waves to the transmission control circuit 33. In a case where the ultrasound wave transmission trigger signal is received, the transmission control circuit 33 makes the probe 11 transmit ultrasound waves. The control unit 34 transmits a sampling trigger signal to the receiving circuit 21 according to the timing of ultrasound wave transmission, thereby starting the sampling of a reflected ultrasound signal.

The receiving circuit 21 receives a detection signal output from the probe 11, and stores the received detection signal in the receiving memory 22. Typically, the receiving circuit 21 is configured to include a low noise amplifier, a variable gain amplifier, a low pass filter, and an AD converter. The detection signal of the probe 11 is amplified by the low noise amplifier, and then gain adjustment according to the depth is performed by the variable gain amplifier and a high-frequency component is cut by the low pass filter. Then, conversion into a digital signal is performed by the AD converter, and the digital signal is stored in the receiving memory 22. The receiving circuit 21 is formed by one integrated circuit (IC), for example.

In the present embodiment, the probe 11 outputs a detection signal of photoacoustic waves and a detection signal of reflected ultrasound waves. Therefore, digitized detection signals (sampling data) of photoacoustic waves and reflected ultrasound waves are stored in the receiving memory 22. The data separation unit 23 reads the sampling data (photoacoustic data) of the photoacoustic wave detection signal from the receiving memory 22, and transmits the sampling data to the photoacoustic image generation unit 24. The data separation unit 23 reads the sampling data (reflected ultrasound data) of the reflected ultrasound detection signal from the receiving memory 22, and transmits the sampling data to the ultrasound image generation unit 29.

The photoacoustic image generation unit 24 reconstructs data of one line by adding the pieces of photoacoustic data stored in the receiving memory 22 to each other with a delay time corresponding to the position of the transducer array 20 of the probe 11, and generates data of a tomographic image (photoacoustic image) based on the photoacoustic data of each line. The photoacoustic image generation unit 24 may perform reconstruction using a circular back projection (CBP) instead of the delay addition method. Alternatively, the photoacoustic image generation unit 24 may perform reconstruction using a Hough transform method or a Fourier transform method. The photoacoustic image generation unit 24 outputs the data of the photoacoustic image generated as described above to the display control unit 30.

The ultrasound image generation unit 29 generates data of a tomographic image (ultrasound image) by performing basically the same processing as for the photoacoustic data on the reflected ultrasound data stored in the receiving memory 22. The ultrasound image generation unit 29 outputs the data of the ultrasound image generated as described above to the display control unit 30.

The display control unit 30 displays a photoacoustic image on the display unit 14 based on the data of the photoacoustic image, and displays an ultrasound image on the display unit 14 based on the data of the ultrasound image. These two images are separately displayed on the display unit 14, or are combined to be displayed on the display unit 14 as a composite image. In the latter case, the display control unit 30 performs image combination by superimposing the photoacoustic image and the ultrasound image, for example. In this manner, if the ultrasound image is generated and displayed in addition to the photoacoustic image, a portion that can not be imaged in the photoacoustic image can be observed in the ultrasound image. Therefore, by using a tissue, such as a bone or a nerve drawn in the ultrasound image, as a landmark, it is possible to understand at which position, for example, a blood vessel or an insertion needle shown in the photoacoustic image is present more easily than in a case where a photoacoustic image is independently observed.

In particular, in the case of acquiring a plurality of tomographic images for constructing a three-dimensional image, in the case of acquiring the photoacoustic image or the ultrasound image described above, the position of the probe 11 is gradually changed in the above-described elevation direction with respect to the subject M, and the subject M is scanned with the laser light L or ultrasound waves. Therefore, sampling of the photoacoustic signal or the reflected ultrasound signal is performed while shifting the acoustic wave detection line line by line in synchronization with the scanning. The scanning may be performed by manually moving the probe 11 by the operator or may be performed using an automatic scanning mechanism.

In the photoacoustic measurement apparatus 10 of the present embodiment, the biopsy needle 15 that is a kind of an insertion needle is provided. The biopsy needle 15 is inserted into the subject M in order to collect a living tissue (biological sample) inside the subject M. The biopsy needle 15 is connected to the laser unit 13 through a light guide member 16, such as an optical fiber. The biopsy needle 15 is configured to include a part of the light guide member 16.

Next, an embodiment of a biopsy needle of the present invention will be described.

First Embodiment of a Biopsy Needle

Figure 2:
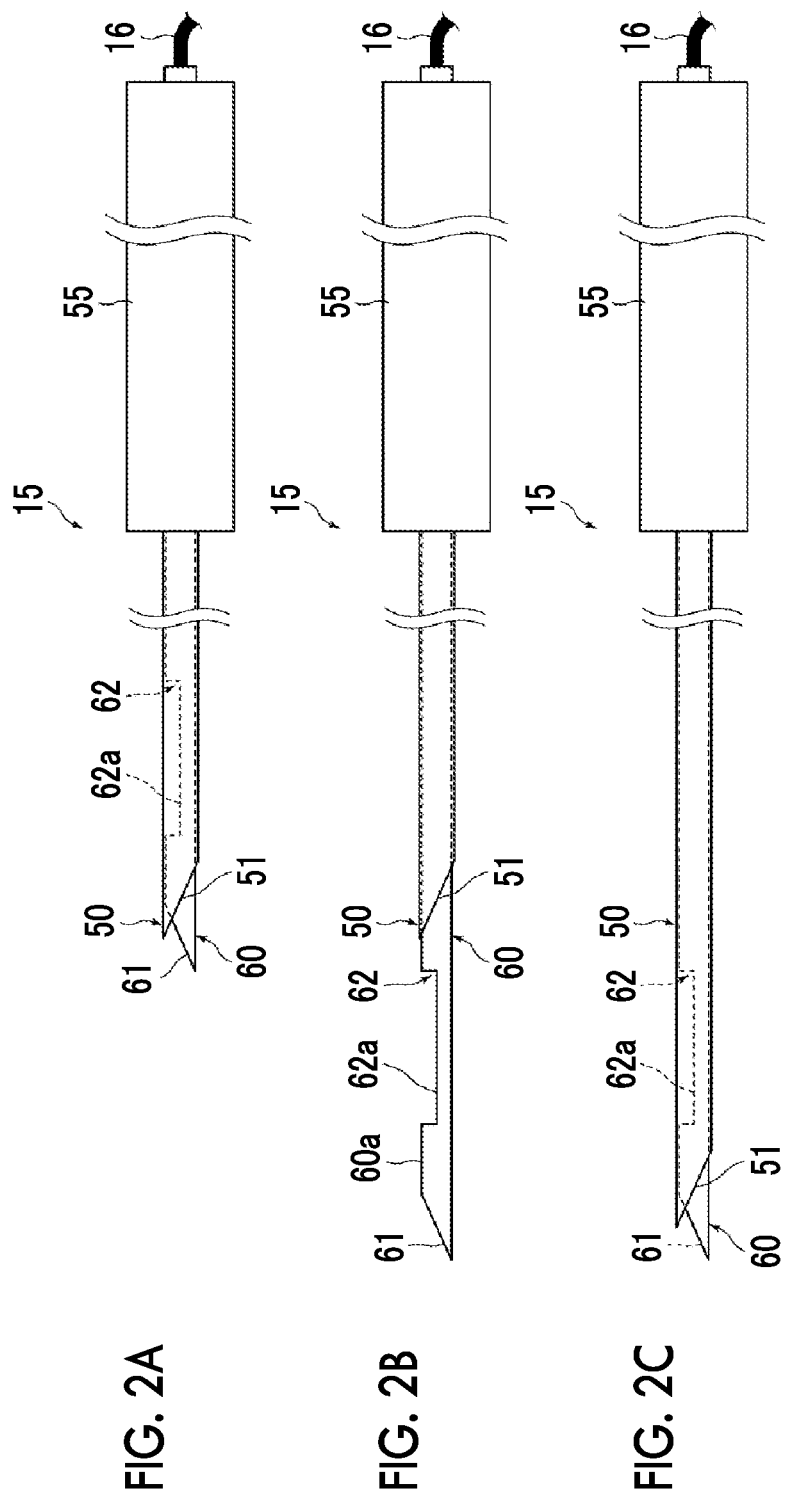
FIGS. 2A to 2C are schematic diagrams showing three states in a case where a biopsy needle according to a first embodiment of the present invention is used.

First, the biopsy needle 15 according to a first embodiment of the present invention will be described. The basic structure of the biopsy needle 15 will be described first with reference to FIGS. 2A to 2C. The biopsy needle 15 has a hollow tubular outer needle 50, which is held by a grip portion (handle) 55 gripped by an operator, and an inner needle 60, which is disposed in the hollow portion (that is, in the hollow tube) of the outer needle 50 so as to be movable in the tube axis direction relative to the outer needle 50. The light guide member 16 formed of an optical fiber or the like is connected to the biopsy needle 15. In FIGS. 2A to 2C, the arrangement state of the light guide member 16 in the biopsy needle 15 is not shown.

The outer needle 50 is formed of, for example, metal, and a distal end 51 of the outer needle 50 is obliquely cut. On the other hand, the inner needle 60 is formed of, for example, a metal member having an approximately cylindrical shape, and a distal end 61 of the inner needle 60 is obliquely cut. The outer needle 50 and the inner needle 60 are combined, for example, in a state in which the directions of cuts of the respective distal ends are different from each other by 180°. The distal end 51 of the outer needle 50 and the distal end 61 of the inner needle 60 are end portions on a side of inserted into the subject M, which is an opposite side to a side where the light guide member 16 is connected. In the inner needle 60, a sample collection portion 62 is provided at a position spaced a predetermined distance from the distal end toward the rear end side. The predetermined distance is appropriately set according to the application, standard, and the like of the biopsy needle. The sample collection portion 62 is a recessed portion cut inward from a circumferential surface 60a of the inner needle 60.

In the grip portion 55, rear end portions of the outer needle 50 and the inner needle 60, that is, end portions of the outer needle 50 and the inner needle 60 on a side where the needle base is mounted are housed. In the grip portion 55, a sliding mechanism (not shown) for moving the outer needle 50 and the inner needle 60 forward and backward is provided. As the sliding mechanism, a manual type sliding mechanism having only a guide mechanism for simply moving the outer needle 50 and the inner needle 60 forward and backward or an automatic type sliding mechanism, which applies insertion force to the outer needle 50 and the inner needle 60 by pushing out the outer needle 50 and the inner needle 60 with the force of a spring, can be appropriately selected and applied. A semi-automatic type sliding mechanism may be applied in which the inner needle 60 is manually pushed out and the outer needle 50 is pushed out with the force of a spring. Instead of the spring force, a sliding mechanism that applies insertion force to the outer needle 50 or the inner needle 60 by compressed gas or electromagnetic force can also be applied.

In the above JP1999-33029A (JP-H11-33029A), an example of a sliding mechanism that operates as described above is also described.

Hereinafter, a biological sample collection operation of the biopsy needle 15 will be described. First, as shown in FIG. 2A, the outer needle 50 and the inner needle 60 are inserted into the subject M (refer to FIG. 1), which is a living body, in a state in which the distal end 51 of the outer needle 50 and the distal end 61 of the inner needle 60 are substantially aligned. In this case, the outer needle 50 and the inner needle 60 are inserted so that the distal ends 51 and 61 are located slightly in front of a sampling part of the subject M. The insertion operation described above is performed by an operator who grips the grip portion 55 of the biopsy needle 15.

Then, as shown in FIG. 2B, the inner needle 60 is moved to the distal end side by the above-described sliding mechanism (moved forward), so that the sample collection portion 62 is moved into the sampling part. Then, as shown in FIG. 2C, the outer needle 50 is moved forward to a position where the distal end 51 exceeds the sample collection portion 62. The forward movement of the outer needle 50 is also performed by the above-described sliding mechanism. Therefore, a biological sample is cut off by the distal end 51 of the outer needle 50, and the cut sample is held in the sample collection portion 62 in the outer needle 50. Then, the outer needle 50 and the inner needle 60 are removed from the subject M, and the outer needle 50 is retracted to the grip portion 55 side. As a result, the sample held by the sample collection portion 62 is taken out.

Figure 3:
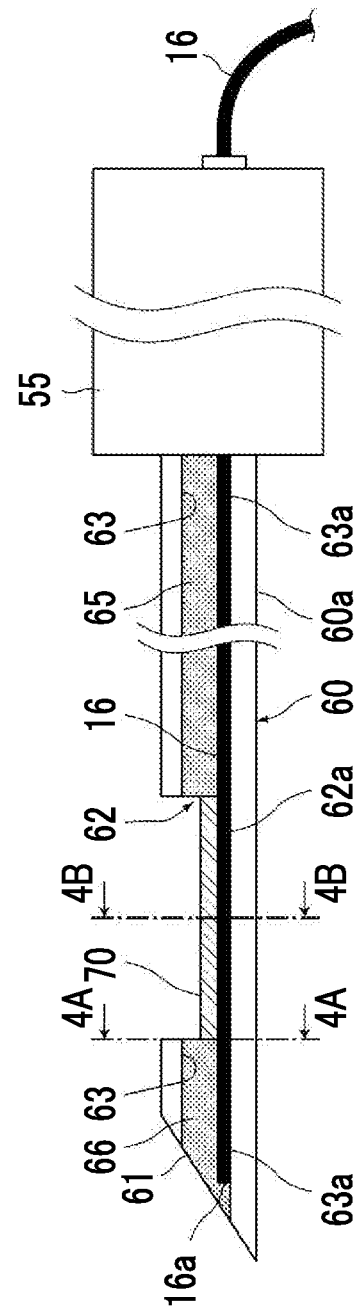
FIG. 3 is a side sectional view showing the biopsy needle according to the first embodiment of the present invention.

Next, the more detailed configuration of the biopsy needle 15 of the present embodiment will be described with reference FIGS. 3, 4A, and 4B. FIG. 3 shows the inner needle 60 of the biopsy needle 15 taken along a plane that is perpendicular to a bottom surface 62a of the sample collection portion 62 and includes the central axis of the inner needle 60. The outer needle 50 is omitted in this diagram. FIGS. 4A and 4B are cross-sectional views taken along the lines 4A-4A and 4B-4B in FIG. 3, respectively, when viewed from the arrow direction. A portion 60a indicated by a broken line in FIG. 4B shows a circumferential surface of the inner needle 60 before the recessed sample collection portion 62, which will be described later, is formed.

On the inner needle distal end side and the inner needle rear end side of the sample collection portion 62 in the inner needle 60, inner holes 63 extending in the tube axis direction (longitudinal direction) of the inner needle are provided. Each of the inner holes 63 is formed coaxially with the inner needle 60, and is opened to the recessed sample collection portion 62. In the present embodiment, the cross-sectional shapes of the inner holes 63 are circular. The inner holes 63 are provided in a state in which bottom surfaces 63a thereof are located at the same height position as the flat bottom surface 62a of the sample collection portion 62. The "height position" refers to top and bottom positions in a vertical direction in a state in which the biopsy needle 15 is disposed such that the bottom surface 62a of the sample collection portion 62 faces the top side in the vertical direction. The bottom surface 62a of the sample collection portion 62 is a surface within the sample collection portion 62 located at the lowest height position, and the bottom surfaces 63a of the inner holes 63 are surfaces within the inner holes 63 similarly located at the lowest height position.

In each of the two inner holes 63, the light guide member 16 (first light guide member) formed of an optical fiber or the like is disposed so as to be located on the bottom surface 63a. The light guide member 16 is located on the bottom surface 62a of the sample collection portion 62 in the sample collection portion 62. The light guide member 16 is disposed such that a distal end 16a is located near the distal end of the inner needle 60. Light is incident on the light guide member 16 from the rear end side (right end side in FIG. 3) as will be described later. The light guide member 16 guides the light so that the light is emitted the distal end 16a. In a case where the light guide member 16 is formed of an optical fiber, the distal end 16a includes a distal end of the core of the optical fiber, and the light is emitted from the distal end of the core.

Here, the phrase "distal end 16a is located near the distal end of the inner needle 60" means that the distal end 16a is present at a position where photoacoustic waves emitted from a light absorber (which will be described later), which has absorbed the light emitted from the distal end 16a of the light guide member 16, can propagate from the distal end 61 of the inner needle 60 to the outside in a state in which the biopsy needle 15 is inserted into the subject M and can be detected by the probe 11 shown in FIG. 1.

As an example, in a case where the outer diameter of a portion of the inner needle 60 where the sample collection portion 62 is not formed is about 0.9 to 1.2 mm and the outer diameter of the light guide member 16 is about 0.1 to 0.2 mm, the diameter of the inner holes 63 are about 0.3 to 0.4 mm.

In terms of easy operation and difficulty of breakage between the laser unit 13 and the grip portion 55, it is preferable that the light guide member 16 is thinner as long as the light guiding property is not adversely affected. On the other hand, the biopsy needle is defined by JIS T3228 "Biopsy needle for living tissue collection". Among these, the thickness of the inner needle is described to ensure rigidity in "A. 1. 2 Thickness of an inner needle having a sample collection space portion for tissue diagnosis". However, there is no particular numerical specification, and the outer diameter of the inner needle 60 is also an example.

Fillers 65 and 66 formed of a synthetic resin are filled in the inner hole 63 on the inner needle rear end side of the sample collection portion 62 and the inner hole 63 on the inner needle distal end side, respectively. The fillers 65 and 66 are filled in the inner holes 63 in a molten state after the light guide member 16 is disposed in the inner holes 63 and are then solidified. The light guide member 16 disposed in each inner hole 63 is covered with the filler 65 and 66 over the entire length of the inner hole 63, and is bonded and fixed to the bottom surface 63a of the inner hole 63. In the present embodiment, particularly the filler 66 on the distal end side of the inner needle 60 is formed of a material that absorbs light emitted from the distal end 16a of the light guide member 16 as will be described later, for example, a synthetic resin, such as an epoxy resin, a fluororesin, or a polyurethane resin mixed with a black pigment.

In the sample collection portion 62, a fixing member 70 that covers the light guide member 16 over the entire length of the sample collection portion 62 is disposed. The fixing member 70 is formed of, for example, synthetic resin. After the light guide member 16 is disposed on the bottom surface 62a of the sample collection portion 62, the fixing member 70 is supplied in a molten state and is then solidified. The light guide member 16 is bonded and fixed onto the bottom surface 62a of the sample collection portion 62 by the fixing member 70.

In the inner hole 63 on the inner needle rear end side of the sample collection portion 62, the filler 65 does not necessarily have to be provided over the entire length of the inner hole, and may be provided only in a part of the entire length of the inner hole 63 (in particular, an end portion of the inner hole in the tube axis direction) so that the light guide member 16 is fixed only by the part. This is the same for the filler 66 in the inner hole 63 on the inner needle distal end side of the sample collection portion 62. However, the filler 66 having a light absorption property is disposed so as to be necessarily present at a position where the distal end 16a of the light guide member 16 is covered. The fixing member 70 may also be provided only in a part of the entire length of the sample collection portion 62 so that the light guide member 16 is fixed only by the part.

The fillers 65 and 66 are generally formed of the same material, but may be formed of different materials. At least one of the filler 65 or the filler 66 and the fixing member 70 may be formed of the same material.

As described above with reference to FIGS. 2A to 2C, in the case of inserting the biopsy needle 15 into the subject M to collect a biological sample, light emitted from the laser unit 13 shown in FIG. 1 is incident on the light guide member 16 from the rear end side (right end side in FIG. 3). In this example, the light is the same laser light L as the light emitted from the probe 11. The light propagates through the light guide member 16, is emitted from the distal end 16a of the light guide member 16, and is absorbed by the filler 66. Photoacoustic waves are emitted from a portion of the filler 66 that has absorbed light, that is, a portion close to the distal end 16a of the light guide member 16. As described above, in the present embodiment, the filler 66 forms a first light absorber in the present invention.

In the case of collecting a biological sample as described above, the laser light L is also emitted from the probe 11 shown in FIG. 1. Accordingly, the photoacoustic image of the subject M is displayed on the display unit 14 as described above. In this case, since the photoacoustic waves are emitted as described above from the portion of the filler 66 close to the distal end 16a of the light guide member 16 and the photoacoustic waves are detected by the probe 11, a photoacoustic image of the portion of the filler 66 is also displayed on the display unit 14. In a case where the photoacoustic image of the portion of the filler 66 close to the distal end 16a of the light guide member 16 is displayed in this manner, the operator can check where the distal end 16a of the light guide member 16, that is, the distal end of the inner needle 60 is located with reference to the display. Therefore, in the case of collecting a biological sample, it is possible to perform safe insertion and appropriate tissue collection.

In a case where the photoacoustic image of the subject M and a portion near the distal end of the inner needle 60 are displayed together on the display unit 14, it is also possible to separately display the absorber 19, such as a blood vessel in the subject M, and the portion near the distal end of the inner needle 60 in different colors. In this manner, the tissue, such as a blood vessel, and the portion near the inner needle distal end can be more clearly distinguished and recognized. As a result, it is possible to safely collect a sample with the inner needle 60 while avoiding the tissue, such as a blood vessel.

Second Embodiment of a Biopsy Needle

Figure 5:
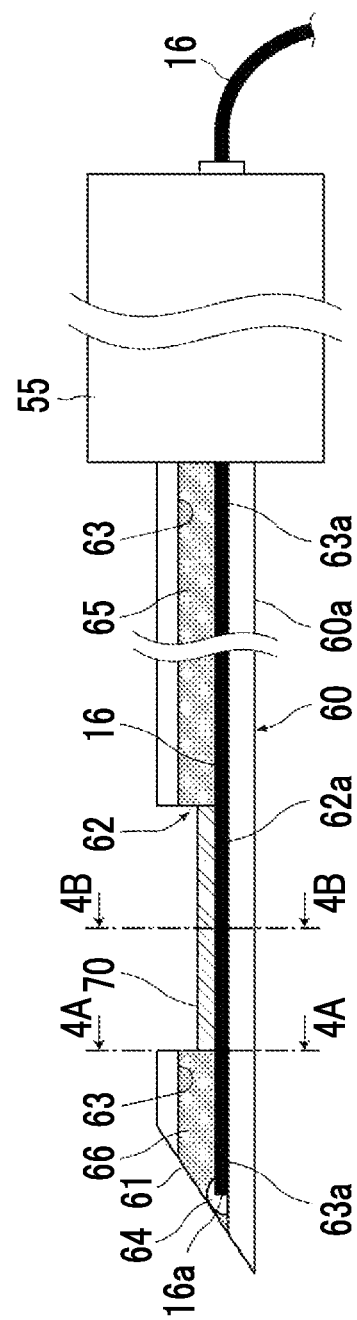
FIG. 5 is a side sectional view showing a biopsy needle according to a second embodiment of the present invention.

Next, a biopsy needle according to a second embodiment of the present invention will be described with reference to FIG. 5. In FIG. 5, the same elements as in FIG. 3 described previously are denoted by the same reference numerals, and the explanation thereof will be omitted unless particularly required (the same hereinbelow).

FIG. 5 is a cross-sectional view showing the inner needle 60, which forms the biopsy needle according to the second embodiment of the present invention, in the same manner as in FIG. 3. The cross-sectional shapes taken along the lines 4A-4A and 4B-4B in FIG. 5 are the same as the cross-sectional shapes in FIGS. 4A and 4B, respectively.

The inner needle 60 shown in FIG. 5 is different from the inner needle 60 shown in FIG. 3 in that a light absorber 64 (first light absorber) is provided so as to cover the distal end 16a of the light guide member 16. As the light absorber 64, a light absorber formed of a synthetic resin, such as an epoxy resin, a fluororesin, or a polyurethane resin mixed with a black pigment, a light absorber containing a metal film or a metal oxide film having a light absorption property, or the like can be applied.

The inner needle 60 shown in FIG. 5 is also combined with the outer needle 50 as shown in FIGS. 2A to 2C to form the biopsy needle 15. Then, in the case of collecting a biological sample using the biopsy needle 15, light is incident on the light guide member 16 from the rear end side (right end side in FIG. 5). The light propagates through the light guide member 16, is emitted from the distal end 16a of the light guide member 16, and is absorbed by the light absorber 64. Photoacoustic waves are emitted from the light absorber 64 that has absorbed the light, and the photoacoustic waves are detected by the probe 11 shown in FIG. 1.

Also in this case, therefore, a photoacoustic image of the light absorber 64 located near the distal end 16a of the light guide member 16 is displayed on the display unit 14 shown in FIG. 1. By referring to this display, the operator can check where the distal end 16a of the light guide member 16, that is, the distal end of the inner needle 60 is located.

Third Embodiment of a Biopsy Needle

Figure 6:
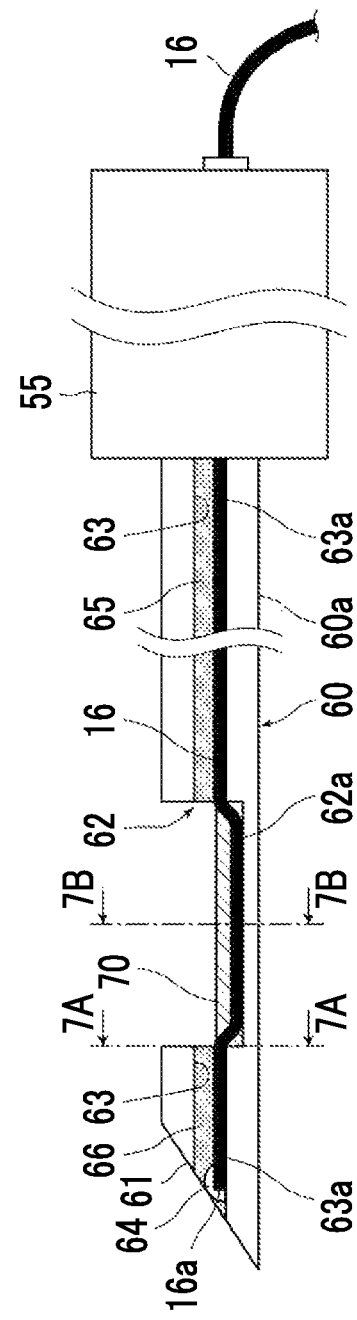
FIG. 6 is a side sectional view showing a biopsy needle according to a third embodiment of the present invention.
Figure 7A:
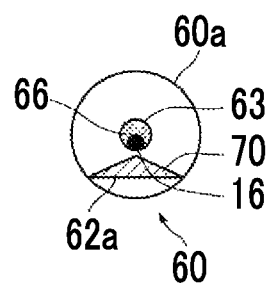
FIGS. 7A and 7B are cross-sectional views of the biopsy needle of the third embodiment taken along the lines 7A-7A and 7B-7B in FIG. 6, respectively.
Figure 7B:
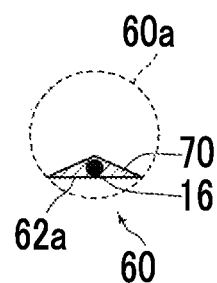

Next, a biopsy needle according to a third embodiment of the present invention will be described with reference to FIGS. 6, 7A, and 7B. FIG. 6 is a cross-sectional view showing the inner needle 60, which forms the biopsy needle according to the third embodiment of the present invention, in the same manner as in FIG. 3. The cross-sectional shapes of the inner needle 60 taken along the lines 7A-7A and 7B-7B in FIG. 6 are shown in FIGS. 7A and 7B, respectively.

The inner needle 60 shown in FIG. 6 is basically different from the inner needle 60 shown in FIG. 3 in that the bottom surface 62a of the sample collection portion 62 is located at a position lower than the bottom surfaces 63a of the inner holes 63. In the present embodiment, the same light absorber 64 as that shown in FIG. 5 is provided. The inner needle 60 shown in FIG. 6 is also combined with the outer needle 50 as shown in FIGS. 2A to 2C to form the biopsy needle 15. Then, in the case of collecting a biological sample using the biopsy needle 15, light is incident on the light guide member 16 from the rear end side (right end side in FIG. 6). Therefore, in the same manner as described above, a photoacoustic image of a portion of the light absorber 64 close to the distal end 16a of the light guide member 16 is displayed on the display unit 14. Also in this case, the filler 66 having a light absorption property may be applied, and the light absorber 64 may be omitted.

In the present embodiment, compared with a case where the bottom surface 62a of the sample collection portion 62 is located at the same height as the bottom surfaces 63a of the inner holes 63 as in the first embodiment, the inner needle 60 of a portion in which the sample collection portion 62 is provided can be made thinner. Therefore, a sample having a larger volume can be collected in the sample collection portion 62.

Fourth Embodiment of a Biopsy Needle

Figure 9A:
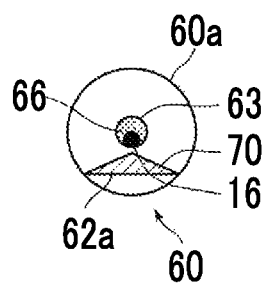
FIGS. 9A and 9B are cross-sectional views of the biopsy needle of the fourth embodiment taken along the lines 9A-9A and 9B-9B in FIG. 8, respectively.
Figure 9B:
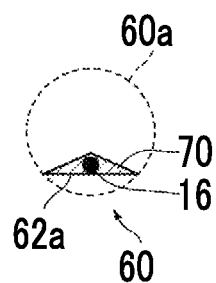

Next, a biopsy needle according to a fourth embodiment of the present invention will be described with reference to FIGS. 8, 9A, and 9B. FIG. 8 is a cross-sectional view showing the inner needle 60, which forms the biopsy needle according to the fourth embodiment of the present invention, in the same manner as in FIG. 3. The cross-sectional shapes of the inner needle 60 taken along the lines 9A-9A and 9B-9B in FIG. 8 are shown in FIGS. 9A and 9B, respectively.

The inner needle 60 shown in FIG. 8 is basically different from the inner needle 60 shown in FIG. 3 in that the bottom surface 62a of the sample collection portion 62 is located at a position lower than the bottom surfaces 63a of the inner holes 63. This point is the same as the inner needle 60 shown in FIG. 6. In the present embodiment, however, unlike the configuration shown in FIG. 6, each end portion 69 on the inner needle distal end side and the inner needle rear end side of the bottom surface 62a of the sample collection portion 62 is an inclined surface whose height changes continuously and is connected to the bottom surface 63a of the inner hole 63. In the present embodiment, the same light absorber 64 as that shown in FIG. 5 is provided.

The inner needle 60 shown in FIG. 8 is also combined with the outer needle 50 as shown in FIGS. 2A to 2C to form the biopsy needle 15. Then, in the case of collecting a biological sample using the biopsy needle 15, light is incident on the light guide member 16 from the rear end side (right end side in FIG. 8). Therefore, in the same manner as described above, a photoacoustic image of a portion of the light absorber 64 close to the distal end 16a of the light guide member 16 is displayed on the display unit 14. Also in this case, the filler 66 having a light absorption property may be applied, and the light absorber 64 may be omitted.

In the present embodiment, compared with a case where the bottom surface 62a of the sample collection portion 62 is located at the same height as the bottom surfaces 63a of the inner holes 63 as in the first embodiment, the inner needle 60 of a portion in which the sample collection portion 62 is provided can be made thinner. Therefore, a sample having a larger volume can be collected in the sample collection portion 62.

In the present embodiment, the end portion 69 of the bottom surface 62a of the sample collection portion 62 is an inclined surface as described above. Therefore, in the case of arranging the light guide member 16 along the bottom surface 62a and the bottom surface 63a of the inner hole 63, it is possible to more smoothly arrange the light guide member 16 by preventing the light guide member 16 from abruptly bending between the bottom surface 62a and the bottom surface 63a. In this manner, in the case of collecting a biological sample with the biopsy needle 15 that is formed by applying the inner needle 60 shown in FIG. 8, it is possible to prevent a large shear force from acting on the light guide member 16 to break the light guide member 16.

An angle of the end portion 69 with respect to the bottom surface 62a of a portion other than the end portion 69 is set to 10° to 30° as an example. Undoubtedly, this angle is not limited to the value, and can be appropriately determined according to the ease of bending of the light guide member 16 or the like. The end portion 69 may be a surface that is inclined while being curved.

Here, the inner holes 63 provided in the inner needle 60 may be formed coaxially with the inner needle 60, or may be formed so as to be eccentric with respect to the inner needle 60. The inner holes 63 may have a cross-sectional shape other than the circular shape, for example, a quadrangular cross-sectional shape.

Fifth Embodiment of a Biopsy Needle

Figure 10:
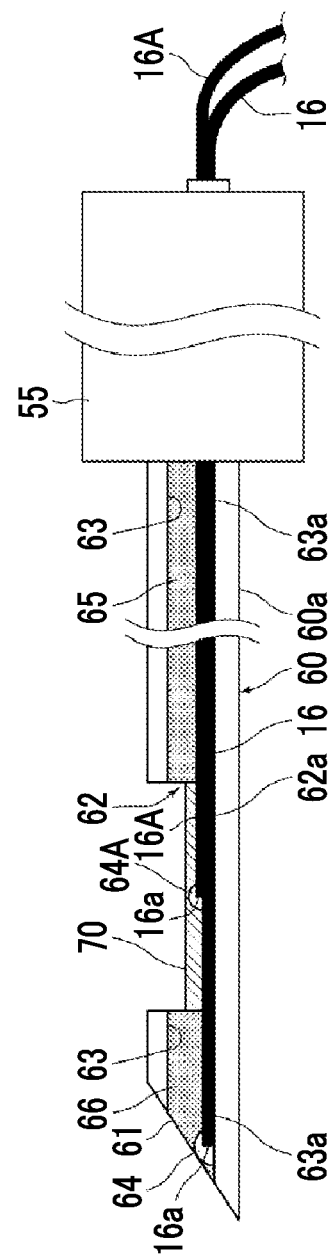
FIG. 10 is a side sectional view showing a biopsy needle according to a fifth embodiment of the present invention.

Next, a biopsy needle according to a fifth embodiment of the present invention will be described with reference to FIG. 10. FIG. 10 is a cross-sectional view showing the inner needle 60, which forms the biopsy needle according to the fifth embodiment of the present invention, in the same manner as in FIG. 3. The inner needle 60 of the present embodiment is different from the inner needle 60 shown in FIG. 3 in that another light guide member 16A (second light guide member) is provided with the distal end being located on the bottom surface 62a of the sample collection portion 62.

Another light guide member 16A is fixed onto the inner hole bottom surface 63a by the filler 65 in the inner hole 63 on the inner needle rear end side of the sample collection portion 62. In the inner hole 63, the two light guide members 16 and 16A are fixed by the filler 65 over the entire length. However, only parts of the two light guide members 16 and 16A may be fixed by the filler 65 in the inner hole 63.

On the bottom surface 62a of the sample collection portion 62, a light absorber 64A (second light absorber) is provided so as to cover the distal end 16a of another light guide member 16A. As the light absorber 64A, a light absorber formed of a synthetic resin, such as an epoxy resin, a fluororesin, or a polyurethane resin mixed with a black pigment, a light absorber containing a metal film or a metal oxide film having a light absorption property, or the like can be applied. Also in the present embodiment, as the filler 66 disposed in the inner hole 63 on the inner needle distal end side of the sample collection portion 62, a filler acting as a light absorber is used. Therefore, in this example, the light absorber 64A is provided as a light absorber different from the filler 66. Instead of providing the light absorber 64A, the fixing member 70 may be formed of a light absorbing material so as to be used as a light absorber.

The inner needle 60 shown in FIG. 10 is also combined with the outer needle 50 as shown in FIGS. 2A to 2C to form the biopsy needle 15. Then, in the case of collecting a biological sample using the biopsy needle 15, light is incident on the two light guide members 16 and 16A from the rear end side (right end side in FIG. 10). The light propagates through the light guide members 16 and 16A, is emitted from the distal ends 16a of the light guide members 16 and 16A, and is absorbed by the filler 66 and the light absorber 64A. Photoacoustic waves are emitted from the filler 66 and the light absorber 64A that have absorbed the light, and the photoacoustic waves are detected by the probe 11 shown in FIG. 1.

Also in this case, therefore, a photoacoustic image of the filler 66 is displayed on the display unit 14 shown in FIG. 1. By referring to this display, the operator can check where the distal end 16a of the light guide member 16, that is, the distal end of the inner needle 60 is located.

In addition to this, a photoacoustic image of the light absorber 64A is also displayed on the display unit 14 shown in FIG. 1. The distance between the distal end 16a of the light guide member 16 covered with the filler 66 and the distal end 16a of the light guide member 16A covered with the light absorber 64A and the distance from the distal end 61 of the inner needle 60 to the sample collection portion 62 are set in advance. Accordingly, the operator can correctly know the position of the sample collection portion 62 with reference to the display of the filler 66 and the light absorber 64A. By knowing the position of the sample collection portion 62 correctly, it is possible to improve the accuracy of collecting the target living tissue.

Sixth Embodiment of a Biopsy Needle

Figure 11:
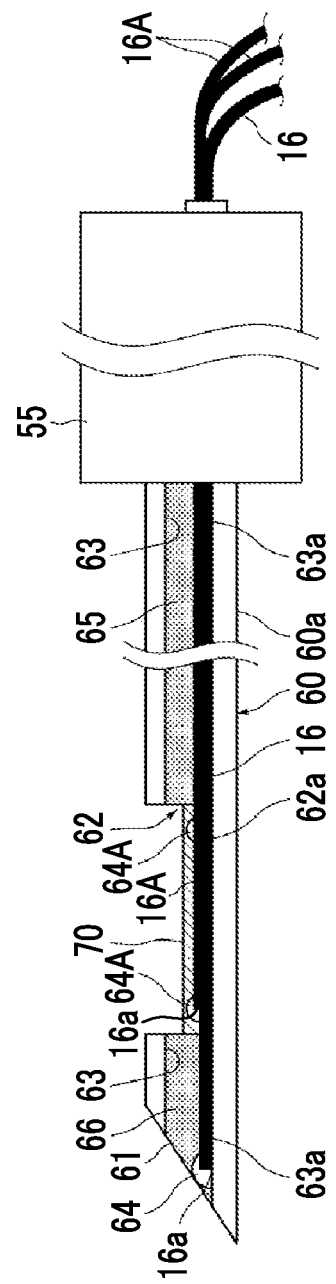
FIG. 11 is a side sectional view showing a biopsy needle according to a sixth embodiment of the present invention.

Next, a biopsy needle according to a sixth embodiment of the present invention will be described with reference to FIG. 11. FIG. 11 is a cross-sectional view showing the inner needle 60, which forms the biopsy needle according to the sixth embodiment of the present invention, in the same manner as in FIG. 3. The inner needle 60 of the present embodiment is different from the inner needle 60 shown in FIG. 10 in that another light guide member 16A (second light guide member) is provided with the distal end being located on the bottom surface 62a of the sample collection portion 62. That is, in this example, a total of three light guide members that are the light guide members 16, 16A, and 16A are provided.

A distal end of each of the two light guide members 16A provided in a state in which the distal end is located on the bottom surface 62a of the sample collection portion 62 is covered with the same light absorber 64A (second light absorber) as that shown in FIG. 10. Therefore, in the case of using the biopsy needle 15 that is formed by applying the inner needle 60 shown in FIG. 11, not only the photoacoustic image of the filler 66 but also photoacoustic images of the two light absorbers 64A are displayed on the display unit 14 shown in FIG. 1. The operator can correctly know the position of the distal end of the inner needle 60 and the position of the sample collection portion 62 with reference to these displays.

Particularly in the present embodiment, the two light absorbers 64A are provided in the sample collection portion 62, and their photoacoustic images are displayed. Therefore, it is possible to correctly know the position of the sample collection portion 62 even if the extension direction of the biopsy needle 15 at the time of sampling is a direction crossing the photoacoustic image surface. By knowing the position of the sample collection portion 62 correctly as described above, it is possible to improve the accuracy of collecting the target living tissue.

Figure 12:
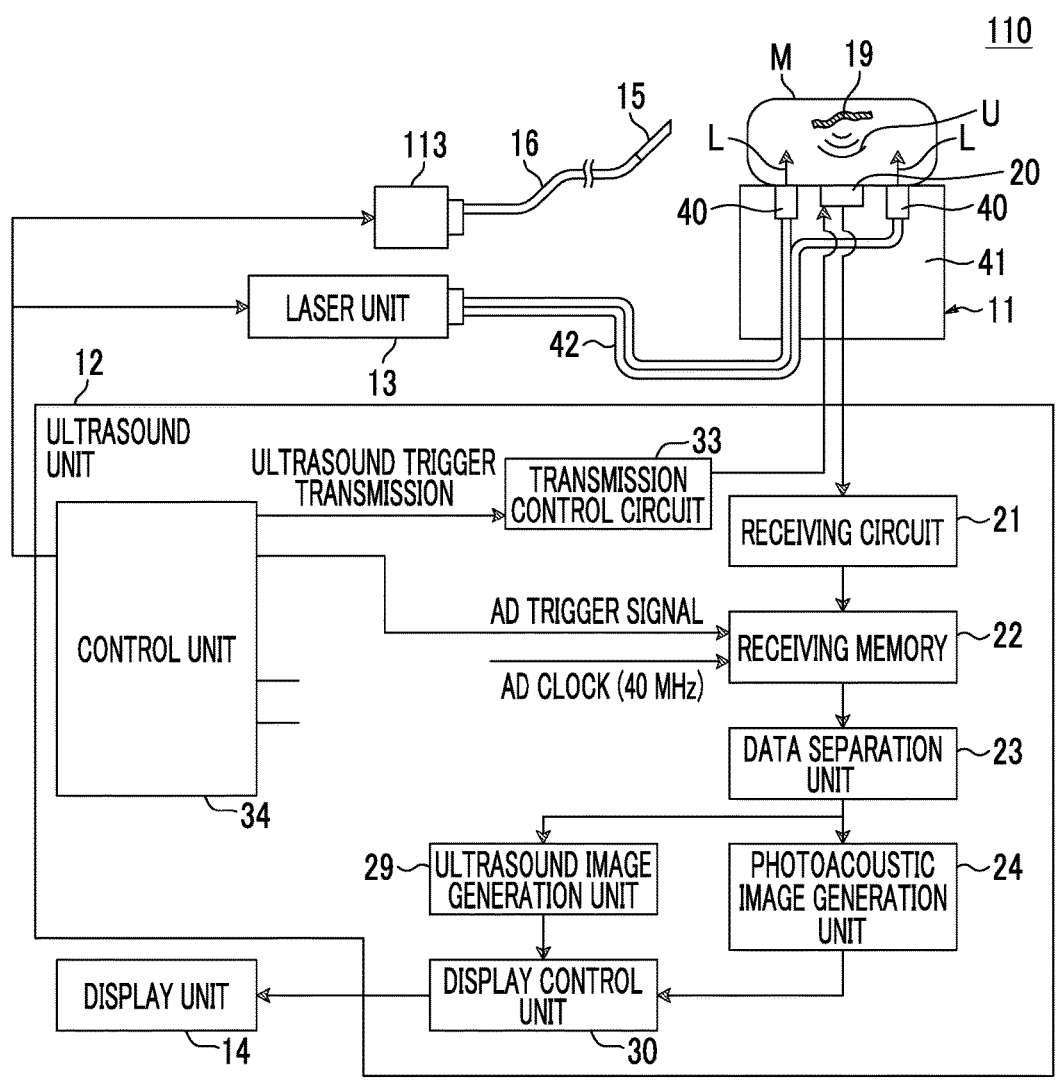
FIG. 12 is a schematic diagram showing the overall configuration of a photoacoustic measurement apparatus according to another embodiment of the present invention.

Here, another embodiment of the photoacoustic measurement apparatus will be described. A photoacoustic measurement apparatus 110 shown in FIG. 12 is basically different from the photoacoustic measurement apparatus 10 shown in FIG. 1 in that not only the relatively high-output laser unit 13 that transmits the laser light L to the probe 11 in order to acquire a photoacoustic image of the subject M but also another laser unit 113 is provided. The laser unit 113 is, for example, a relatively low-output laser light source, such as a laser diode (LD) or a light emitting diode (LED). In this example, the driving of the laser unit 113 is controlled by the control unit 34 that controls the driving of the laser unit 13. However, the present invention is not limited thereto, and the driving of the laser unit 113 may be controlled by another control unit other than the control unit 34.

The laser light emitted from the laser unit 113 is guided by the light guide member 16 and is transmitted to the biopsy needle 15. As the biopsy needle 15, any of the biopsy needles according to the first to sixth embodiments described above may be applied.

Thus, in a case where different light sources, that is, the laser unit 13 and the laser unit 113 are used for acquisition of a photoacoustic image showing blood vessels and the like in the subject M and acquisition of a photoacoustic image showing a biopsy needle distal end portion, these light sources can be driven independently of each other. In this case, therefore, the former photoacoustic image and the latter photoacoustic image can be separately acquired and displayed. In a case where blood vessels or the like and the biopsy needle distal end portion are displayed together in one photoacoustic image, the display of the biopsy needle distal end portion overlaps the display of the blood vessels or the like. Accordingly, it may be difficult to check the biopsy needle distal end portion. In the present embodiment, however, it is possible to prevent the occurrence of such a problem.

In order to obtain the above effect, a single light source, such as a laser unit, may be provided and a shutter may be provided in each optical path after light emitted from the light source is branched so as to follow two optical paths, so that the light is selectively transmitted to either the probe 11 or the biopsy needle 15 by opening and closing these shutters. In such a case, the opening and closing states of the two shutters may be kept unchanged until the acquisition of a photoacoustic image showing the absorber 19, such as a blood vessel in the subject M, or the acquisition of a photoacoustic image showing the distal end portion of the biopsy needle 15 is completed, or a photoacoustic wave detection signal relevant to the former photoacoustic image and a photoacoustic wave detection signal relevant to the latter photoacoustic image may be alternately changed and acquired by switching the opening and closing states of the two shutters within a short time.

In order to make light reach a deep portion of the subject M from the body surface through the probe 11, higher-output light is required than in a case where light is transmitted to the vicinity of the distal end of the biopsy needle 15 through a light guide unit. That is, this is because, in the former case, the light attenuates within the subject M before reaching the deep portion. Then, the photoacoustic wave detection signal becomes weak. In contrast, in the latter case, although there is a loss in the light guide unit, such as an optical fiber, there is no large attenuation of the light due to the subject M. Therefore, as described above, a relatively low-output laser light source, such as a laser diode (LD) or a light emitting diode (LED), can be applied.

Figure 13:
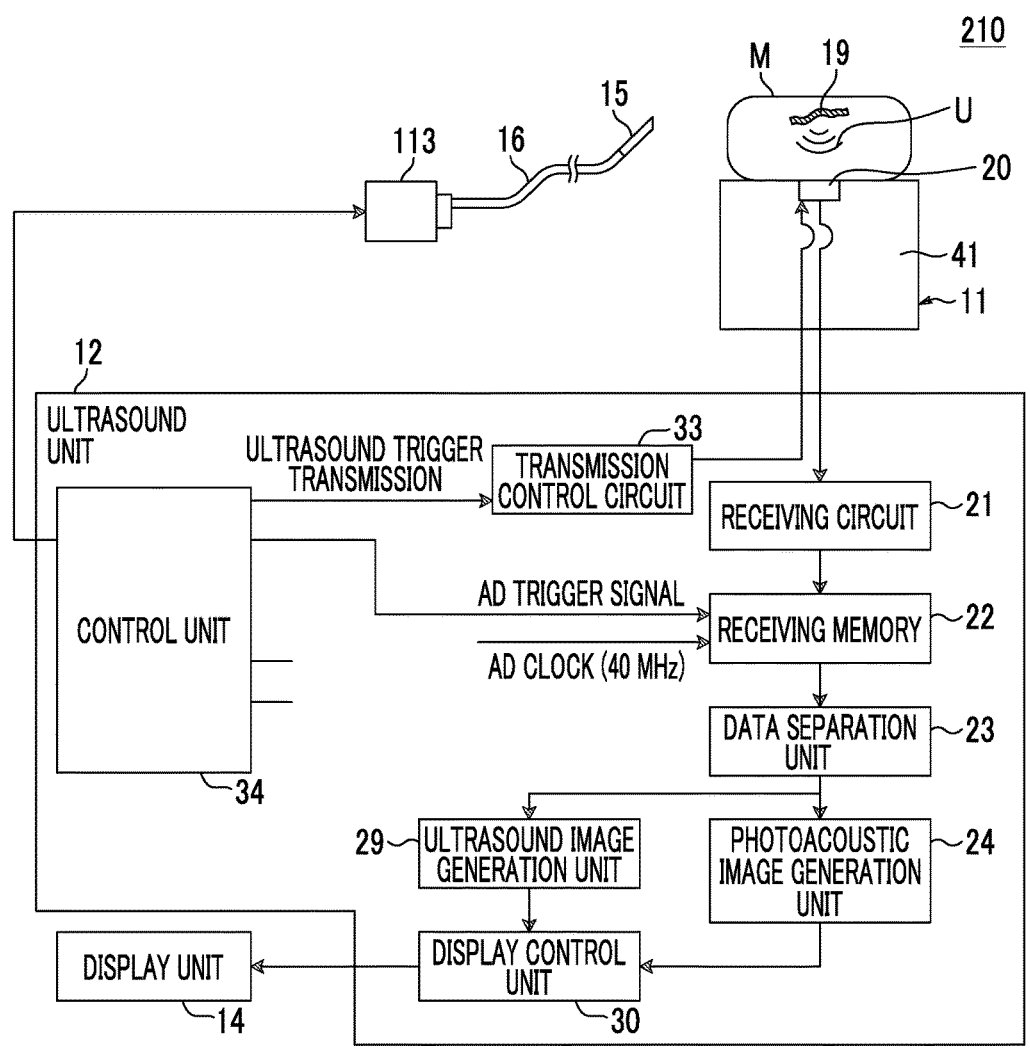
FIG. 13 is a schematic diagram showing the overall configuration of a photoacoustic measurement apparatus according to still another embodiment of the present invention.

Next, still another embodiment of the photoacoustic measurement apparatus will be described. A photoacoustic measurement apparatus 210 shown in FIG. 13 is different from the photoacoustic measurement apparatus 110 shown in FIG. 12 in that a configuration for acquiring a photoacoustic image of the subject M, that is, the laser unit 13, the optical fiber 42, and the light emitting unit 40, are omitted. That is, the probe 11 in the present embodiment does not have a light emission function.

In the photoacoustic measurement apparatus 210, only an ultrasound image of the subject M is acquired without acquiring a photoacoustic image thereof. Therefore, a photoacoustic image showing the vicinity of the distal end of the biopsy needle 15 is displayed on the display unit 14 so as to overlap the ultrasound image of the subject M.

Since the photoacoustic measurement apparatus 210 having the above-described configuration can be formed simply by adding the laser unit 113, the light guide member 16, and program software for photoacoustic image acquisition to the existing ultrasound image acquisition apparatus, it is possible to cope with the request for checking the distal end of the biopsy needle at low cost.

EXPLANATION OF REFERENCES 10, 110, 210: photoacoustic measurement apparatus
11: probe
12: ultrasound unit
13, 113: laser unit
14: display unit
15: biopsy needle
16: light guide member (first light guide member)
16A: light guide member (second light guide member)
20: transducer array
21: receiving circuit
22: receiving memory
23: data separation unit
24: photoacoustic image generation unit
29: ultrasound image generation unit
30: display control unit
33: transmission control circuit
34: control unit
40: light emitting unit
42: optical fiber
50: outer needle
51: distal end of an outer needle
60: inner needle
61: distal end of an inner needle
62: sample collection portion
62a: bottom surface of sample collection portion
63: inner hole
63a: bottom surface of inner hole
64: light absorber (first light absorber)
64A: light absorber (second light absorber)
65, 66: filler
70: fixing member
L: laser light
M: subject
U: acoustic wave

What is claimed is:

1. A biopsy needle, comprising:
a hollow tubular outer needle;
an inner needle that is movable in a tube axis direction relative to the outer needle and that is disposed in a hollow tube of the outer needle;
a sample collection portion that has a recessed shape and that is provided on a circumferential surface of the inner needle;
an inner hole that is provided on each of a distal end side and a rear end side of the sample collection portion in the inner needle and that extends in the tube axis direction of the inner needle;
a first light guide member that is disposed in the inner hole and that is disposed from the rear end side of the inner needle to vicinity of the distal end of the inner needle;
a first light absorber that absorbs light emitted from a distal end of the first light guide member and emits a photoacoustic wave; and
a filler that is filled in the inner hole to fix at least a part of the first light guide member.

2. The biopsy needle according to claim 1,
wherein the first light guide member is fixed to a bottom surface of the sample collection portion by a fixing member that covers at least a part of the first light guide member.

3. The biopsy needle according to claim 1,
wherein a bottom surface of the inner hole and a bottom surface of the sample collection portion are located at the same height position.

4. The biopsy needle according to claim 2,
wherein a bottom surface of the inner hole and the bottom surface of the sample collection portion are located at the same height position.

5. The biopsy needle according to claim 1,
wherein a bottom surface of the sample collection portion is located at a position lower than a bottom surface of the inner hole.

6. The biopsy needle according to claim 2,
wherein the bottom surface of the sample collection portion is located at a position lower than a bottom surface of the inner hole.

7. The biopsy needle according to claim 5,
wherein at least one of an end portion of the bottom surface of the sample collection portion on an inner needle distal end side or an end portion of the bottom surface of the sample collection portion on an inner needle rear end side has an inclined surface whose height changes continuously.

8. The biopsy needle according to claim 6,
wherein at least one of an end portion of the bottom surface of the sample collection portion on an inner needle distal end side or an end portion of the bottom surface of the sample collection portion on an inner needle rear end side has an inclined surface whose height changes continuously.

9. The biopsy needle according to claim 1,
wherein the filler filled in the inner hole provided on the distal end side of the sample collection portion in the inner needle also serves as the first light absorber.

10. The biopsy needle according to claim 2,
wherein the filler filled in the inner hole provided on the distal end side of the inner needle the sample collection portion in the inner needle also serves as the first light absorber.

11. The biopsy needle according to claim 3,
wherein the filler filled in the inner hole provided on the distal end side of the inner needle the sample collection portion in the inner needle also serves as the first light absorber.

12. The biopsy needle according to claim 4,
wherein the filler filled in the inner hole provided on the distal end side of the inner needle the sample collection portion in the inner needle also serves as the first light absorber.

13. The biopsy needle according to claim 5,
wherein the filler filled in the inner hole provided on the distal end side of the inner needle the sample collection portion in the inner needle also serves as the first light absorber.

14. The biopsy needle according to claim 6,
wherein the filler filled in the inner hole provided on the distal end side of the inner needle the sample collection portion in the inner needle also serves as the first light absorber.

15. The biopsy needle according to claim 7,
wherein the filler filled in the inner hole provided on the distal end side of the inner needle the sample collection portion in the inner needle also serves as the first light absorber.

16. The biopsy needle according to claim 8,
wherein the filler filled in the inner hole provided on the distal end side of the inner needle the sample collection portion in the inner needle also serves as the first light absorber.

17. The biopsy needle according to claim 1, further comprising:
a second light guide member that is disposed in the inner hole provided on the rear end side of the sample collection portion in the inner needle and that has a distal end located in the sample collection portion; and
a second light absorber that absorbs light emitted from the distal end of the second light guide member and emits a photoacoustic wave.

18. The biopsy needle according to claim 17,
wherein the second light guide member is fixed to a bottom surface of the sample collection portion by a fixing member that covers at least a part of the second light guide member.

19. The biopsy needle according to claim 18,
wherein the fixing member also serves as the second light absorber.

20. A photoacoustic measurement apparatus, comprising:
the biopsy needle according to claim 1.

* * * * *